United States Patent

Koblish et al.

(10) Patent No.: US 9,486,280 B2
(45) Date of Patent: Nov. 8, 2016

(54) STEERABLE ABLATION DEVICE WITH LINEAR IONICALLY CONDUCTIVE BALLOON

(71) Applicant: BOSTON SCIENTIFIC SCIMED, INC., Maple Grove, MN (US)

(72) Inventors: Josef V. Koblish, Sunnyvale, CA (US); Raj Subramaniam, Fremont, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 302 days.

(21) Appl. No.: 14/194,440

(22) Filed: Feb. 28, 2014

(65) Prior Publication Data

US 2014/0276811 A1    Sep. 18, 2014

Related U.S. Application Data

(60) Provisional application No. 61/780,911, filed on Mar. 13, 2013.

(51) Int. Cl.
| | | |
|---|---|---|
| A61B 18/18 | (2006.01) | |
| A61B 18/14 | (2006.01) | |
| A61B 18/12 | (2006.01) | |
| A61B 17/00 | (2006.01) | |
| A61B 18/00 | (2006.01) | |

(52) U.S. Cl.
CPC ....... *A61B 18/1492* (2013.01); *A61B 18/1206* (2013.01); *A61B 18/18* (2013.01); *A61B 2017/00323* (2013.01); *A61B 2018/0022* (2013.01); *A61B 2018/00077* (2013.01); *A61B 2018/00083* (2013.01); *A61B 2018/00791* (2013.01); *A61B 2018/00839* (2013.01)

(58) Field of Classification Search
CPC .............. A61B 18/1492; A61B 2018/00577; A61B 2018/00214; A61B 5/6853; A61B 2018/0022
See application file for complete search history.

(56) References Cited

U.S. PATENT DOCUMENTS

| | | | |
|---|---|---|---|
| 5,800,482 A | 9/1998 | Pomeranz et al. | |
| 5,830,213 A | 11/1998 | Panescu et al. | |
| 5,871,483 A | 2/1999 | Jackson et al. | |
| 6,290,697 B1 | 9/2001 | Tu et al. | |
| 6,475,213 B1 * | 11/2002 | Whayne ............. | A61B 18/1492 600/374 |
| 6,491,710 B2 | 12/2002 | Satake | |

(Continued)

FOREIGN PATENT DOCUMENTS

| | | |
|---|---|---|
| EP | 1547537 A1 | 6/2005 |
| EP | 1690564 A1 | 8/2006 |

(Continued)

OTHER PUBLICATIONS

International Preliminary Report on Patentabiiity issued in PCT/US2014/019652, mailed Sep. 24, 2015, 6 pages.

(Continued)

*Primary Examiner* — Jocelyn D Ram
(74) *Attorney, Agent, or Firm* — Faegre Baker Daniels LLP

(57) ABSTRACT

Devices, systems, and methods for performing ablation therapy on body tissue are disclosed. An example ablation device for treating body tissue includes an ionically conductive balloon and a radio-frequency electrode that delivers RF energy into a distal section of the balloon. The balloon can have a composite structure with a non-conductive section and a conductive section. The ablation device can have a steering mechanism configured to deflect the balloon.

19 Claims, 5 Drawing Sheets

(56) References Cited

U.S. PATENT DOCUMENTS

| | | | |
|---|---|---|---|
| 6,500,174 B1* | 12/2002 | Maguire | A61B 18/1492 606/41 |
| 6,529,756 B1* | 3/2003 | Phan | A61B 18/1492 600/374 |
| 6,547,788 B1 | 4/2003 | Maguire et al. | |
| 6,640,120 B1* | 10/2003 | Swanson | A61B 18/1492 600/374 |
| 6,656,174 B1 | 12/2003 | Hegde et al. | |
| 6,923,808 B2 | 8/2005 | Taimisto | |
| 6,932,811 B2 | 8/2005 | Hooven et al. | |
| 6,952,615 B2 | 10/2005 | Satake | |
| 7,112,198 B2 | 9/2006 | Satake | |
| 7,736,362 B2 | 6/2010 | Eberl et al. | |
| 9,037,259 B2* | 5/2015 | Mathur | A61B 18/18 606/32 |
| 2001/0007071 A1* | 7/2001 | Koblish | A61B 18/1492 606/41 |
| 2005/0059965 A1* | 3/2005 | Eberl | A61B 18/1492 606/41 |
| 2005/0065506 A1 | 3/2005 | Phan | |
| 2005/0203597 A1* | 9/2005 | Yamazaki | A61B 18/1492 607/98 |
| 2005/0273095 A1* | 12/2005 | Taimisto | A61B 18/1492 606/41 |
| 2006/0184106 A1* | 8/2006 | McDaniel | A61B 18/1492 604/95.04 |
| 2007/0083192 A1* | 4/2007 | Welch | A61B 18/1492 606/41 |
| 2008/0161795 A1 | 7/2008 | Wang et al. | |
| 2009/0062790 A1 | 3/2009 | Malchano et al. | |
| 2009/0259274 A1 | 10/2009 | Simon et al. | |
| 2011/0125143 A1 | 5/2011 | Gross et al. | |
| 2012/0029511 A1* | 2/2012 | Smith | A61B 18/1492 606/41 |
| 2012/0130363 A1 | 5/2012 | Kim et al. | |
| 2013/0066312 A1* | 3/2013 | Subramaniam | A61B 18/1492 606/33 |
| 2013/0066315 A1* | 3/2013 | Subramaniam | A61B 18/1492 606/41 |
| 2013/0172872 A1* | 7/2013 | Subramaniam | A61B 18/18 606/33 |
| 2013/0172877 A1* | 7/2013 | Subramaniam | A61B 18/1492 606/41 |
| 2014/0074083 A1* | 3/2014 | Horn | A61B 18/18 606/33 |
| 2014/0088586 A1* | 3/2014 | Davis | A61B 18/1492 606/33 |

FOREIGN PATENT DOCUMENTS

| | | |
|---|---|---|
| WO | 0029062 A2 | 5/2000 |
| WO | 0205868 A2 | 1/2002 |
| WO | 0209599 A2 | 2/2002 |
| WO | 0219934 A1 | 3/2002 |
| WO | 2007079278 A1 | 7/2007 |
| WO | 2014158727 A1 | 10/2014 |

OTHER PUBLICATIONS

International Search Report and Written Opinion issued in PCT/US2014/019652, mailed Jun. 20, 2014, 9 pages.

* cited by examiner

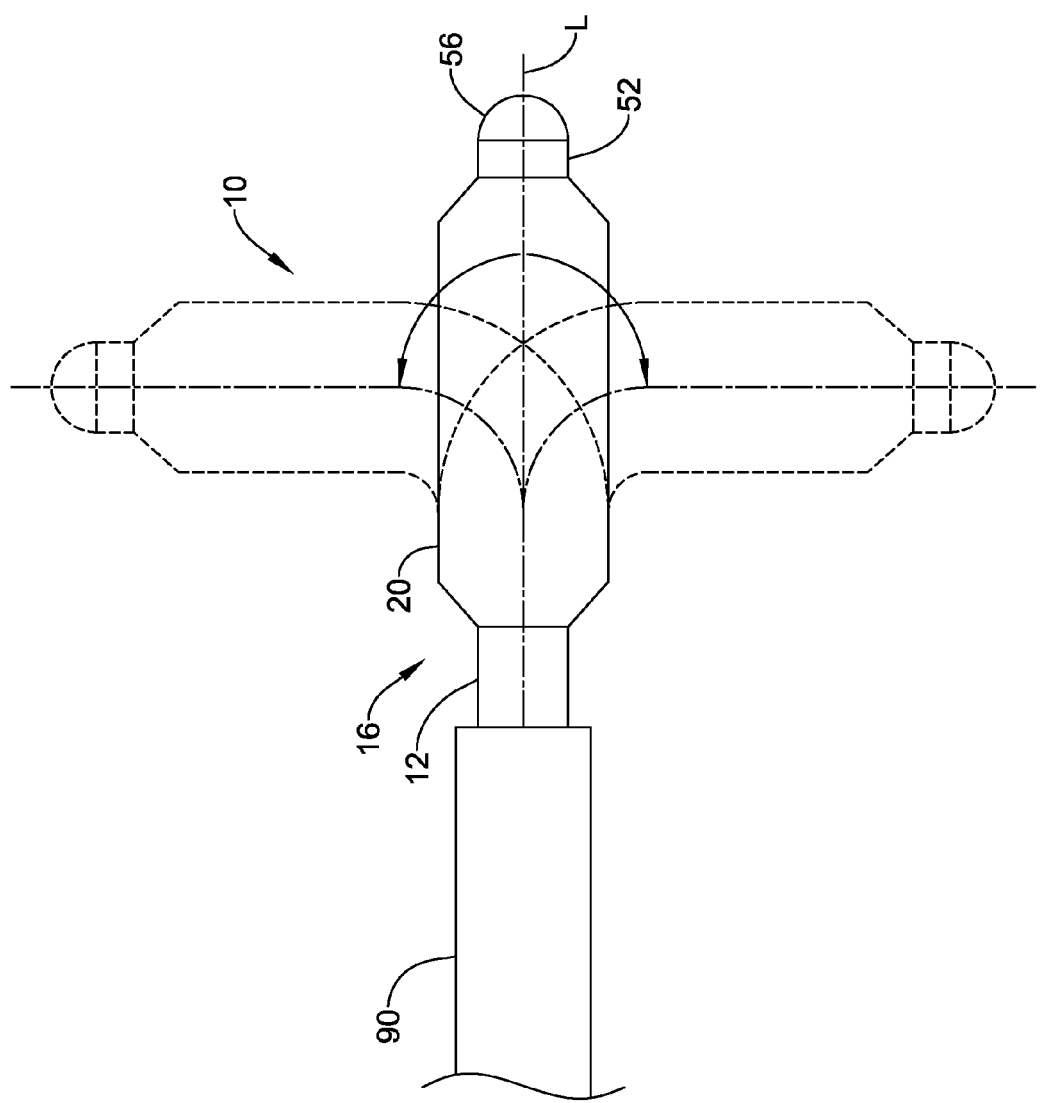

STEERABLE ABLATION DEVICE WITH LINEAR IONICALLY CONDUCTIVE BALLOON

CROSS-REFERENCE TO RELATED APPLICATIONS

This application claims priority under 35 U.S.C. §119 to U.S. Provisional Application Ser. No. 61/780,911, filed Mar. 13, 2013, the entirety of which is incorporated herein by reference.

TECHNICAL FIELD

The present disclosure relates generally to an ablation device. More specifically, the present disclosure pertains to a steerable ablation device including an ionically conductive balloon for performing radio-frequency ablation therapy on body tissue.

BACKGROUND

The treatment of cardiac arrhythmias is sometimes performed in conjunction with an ablation catheter inserted into a chamber of the heart or in one of the vessels leading into or from the heart. In the treatment of atrial fibrillation, for example, a radio frequency (RF) ablation catheter equipped with a number of electrodes can be brought into contact with cardiac tissue for creating one or more ablation points along the tissue. During ablation, an RF generator supplies electrical energy to the electrodes. As the RF energy from the tip electrode pass through the contacting tissue to the ground pad, heat is generated in the tissue. The resulting heat from this electric field forms a controlled lesion that blocks the electrical impulses from being conducted through the tissue and serves to promote the normal conduction of electrical impulses through the proper electrical pathway within the heart.

In certain ablation procedures, it may be difficult to electrically isolate the tissue to be treated with a point ablation catheter. In the treatment of paroxysmal atrial fibrillation, for example, it is often tedious and time consuming to isolate the pulmonary veins using an ablation catheter having an ablation electrode that directly contacts the tissue. Moreover, the ablations created by metal ablation electrodes can cause dehydration in the tissue, which can result in scarring and calcification as the lesion heals. Due to the discrete nature of the ablation points, there is also the potential for leaving small gaps of electrically conductive tissue in the ablation line that may continue to initiate points of arrhythmias.

SUMMARY

The disclosure relates generally to an ablation device including an ionically conductive balloon for performing radio-frequency ablation therapy on body tissue. Accordingly, one illustrative embodiment is an ablation device for treating body tissue including an elongate shaft having a proximal section, a distal section and at least one fluid lumen configured to receive an electrically conductive fluid. A steering mechanism may be disposed within the elongate shaft. The device may further include an inflatable balloon coupled to the distal section of the shaft and including an interior section in fluid communication with the at least one fluid lumen for actuating the balloon between a collapsed state and an expanded state. At least a portion of the balloon may comprise a hydrophilic polymeric material. The device may further include at least one electrode located within the interior space of the balloon.

Another illustrative embodiment is an ablation device for treating body tissue including an elongate shaft having a proximal section, a distal section, a first fluid lumen, and a second fluid lumen. A steering mechanism may be disposed within the elongate shaft. The device may further include an inflatable balloon coupled to the distal section of the shaft and including an interior section in fluid communication with the at least one fluid lumen for actuating the balloon between a collapsed state and an expanded state. A first portion of the balloon may comprise a hydrophilic polymeric material and a second portion of the balloon may comprise a hydrophobic polymeric material. The device may further include at least one electrode located within the interior space of the balloon.

Another illustrative embodiment is an ablation device for treating body tissue including a sheath and an elongate shaft having a proximal section, a distal section, at first fluid lumen, and a second fluid lumen. A steering mechanism may be disposed within the elongate shaft. The steering mechanism may include a steering tube and a center support extending through a lumen of the steering tube. The center support may include a tapered region. A first pull wire may be positioned on a first side of the center support and a second pull wire may be positioned on a second side of the center support. The steering mechanism may further include a compression coil extending along at least a portion of the steering tube. The ablation device may further include an inflatable balloon coupled to the distal section of the shaft and including an interior section in fluid communication with the at least one fluid lumen for actuating the balloon between a collapsed state and an expanded state. A first portion of the balloon may comprise a hydrophilic polymeric material. The device may further include at least one electrode located within the interior space of the balloon.

The above summary of some example embodiments is not intended to describe each disclosed embodiment or every implementation of the invention.

BRIEF DESCRIPTION OF THE DRAWINGS

The invention may be more completely understood in consideration of the following detailed description of various embodiments in connection with the accompanying drawings, in which:

FIG. 5 is a side view of the illustrative ablation device deflected into different configurations.

Figure 1:
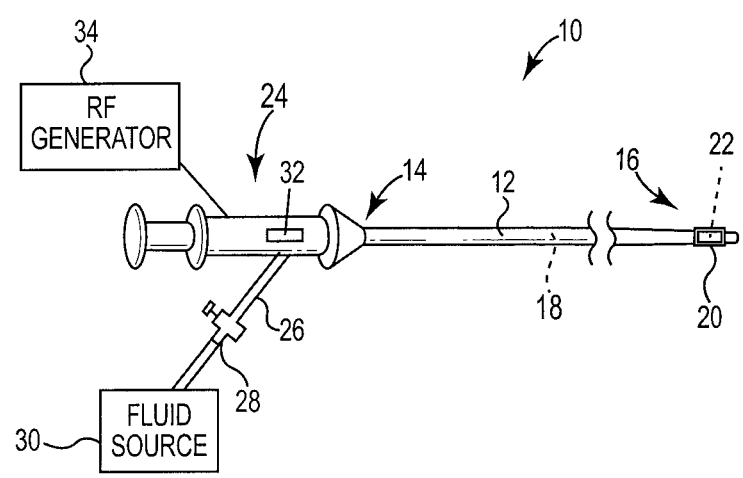
FIG. 1 is a schematic view of an ablation device in accordance with an illustrative embodiment.

While the invention is amenable to various modifications and alternative forms, specifics thereof have been shown by way of example in the drawings and will be described in detail. It should be understood, however, that the intention is not to limit aspects of the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

For purposes of this disclosure, "proximal" refers to the end closer to the device operator during use, and "distal" refers to the end farther from the device operator during use.

The following detailed description should be read with reference to the drawings in which similar elements in different drawings are numbered the same. The detailed description and the drawings, which are not necessarily to scale, depict illustrative embodiments and are not intended to limit the scope of the invention. The illustrative embodiments depicted are intended only as exemplary. Selected features of any illustrative embodiment may be incorporated into an additional embodiment unless clearly stated to the contrary.

FIG. 1 is a schematic view of an ablation device 10 in accordance with an illustrative embodiment. As shown in FIG. 1, the ablation device 10 includes an elongate shaft 12 having a proximal section 14, a distal section 16, and at least one lumen 18 extending through the shaft 12 between the proximal and distal sections 14, 16. An inflatable ablation balloon 20 coupled to the distal section 16 of the shaft 12 can be inflated at a target location within the body (e.g., within a cardiac vessel) and brought into contact with the body tissue to be treated. In some embodiments, and as further described below, an RF electrode assembly 22 located within an interior portion of the balloon 20 generates an RF electric field that can be used for creating controlled lesions within the tissue. In the treatment of paroxysmal atrial fibrillation, for example, the balloon 20 and RF electrode 22 can be used for performing electrical isolation within a pulmonary vein to prevent the aberrant conduction of electrical signals within the left side of the heart. The ablation device 10 can also be used for treating other types of cardiac arrhythmias and/or cardiovascular diseases within the body. The ablation device 10 can also be used for treating other conditions commonly performed by ablation devices. For example, the devices and methods described herein can be applied to renal nerve ablation, hyperplastic tissue ablation, tumor ablation, benign prostatic hyperplasia therapy, nerve excitation or blocking or ablation, modulation of muscle activity, hyperthermia or other warming of tissues, etc.

A handle 24 coupled to the proximal section 14 of the shaft 12 can be used by the clinician for manipulating and steering the balloon 20 to a target site within the body for performing an ablation. In some embodiments, the handle 24 includes a fluid port 26 and valve 28 in fluid communication with a source of electrically conductive fluid 30. In some embodiments, for example, the fluid 30 can comprise saline or a solution of saline and a fluoroscopic contrast medium that is both conductive and biocompatible. During an ablation procedure, pressurized fluid 30 can be delivered via the fluid lumen 18 to the interior of the balloon 20, causing the balloon 20 to inflate while also creating an electrical pathway between the electrode 22 and the portion of the balloon 20 in contact with the body tissue to be treated. In some embodiments, multiple fluid ports can be provided to recirculate the fluid 30 through the ablation device 10 as part of a closed-loop system for controlling the temperature within the balloon 20.

In some embodiments, the ablation device 10 further includes a steering mechanism 32 that can be used to mechanically steer the balloon 20 within the body. In certain embodiments, for example, the steering mechanism 32 comprises an actuation mechanism, such as, but not limited to a slider or lever mechanism, on the handle 24 that can be actuated by the clinician to engage a number of steering wires located within the shaft 12. During delivery of the device 10 to a target region within the body, the steering mechanism 32 can be engaged to deflect the distal end region of the balloon 20, allowing the clinician to better navigate the device 10 through the vasculature and providing improved control over the location of the formed lesions. In some embodiments, the ablation device 10 may be advanced through the vasculature along with a steerable sheath. In such an instance, the ablation device 10 may be disposed within a lumen of the steerable sheath. The steerable sheath may provide macro steering during advancement through the vasculature. Once the ablation device 10 is disposed adjacent to the target region, the steerable sheath may be proximally retracted. The steering mechanism 32 provided with the ablation device 10 may then be used steer the distal end of the balloon 20 in order place the balloon 20 in contact with the desired treatment location, as will be discussed in more detail below.

An RF generator 34 is configured to supply radio-frequency (RF) energy to the electrode assembly 22. In some embodiments, the device 10 is configured to operate in a bipolar mode, in which ablation energy supplied by the RF generator 34 flows from one electrode of the electrode assembly 22 to another electrode of the electrode assembly 22 or provided at a different location along the device 10 (e.g., along the distal section 16 of the shaft 12). In other embodiments, the device 10 is configured to operate in a unipolar mode and/or monopolar mode, in which an indifferent electrode (e.g., an electrode patch) is attached to the patient's back or other exterior skin area and ablation energy from the RF generator 34 flows from one electrode of the assembly 22 to the indifferent electrode.

Figure 2:
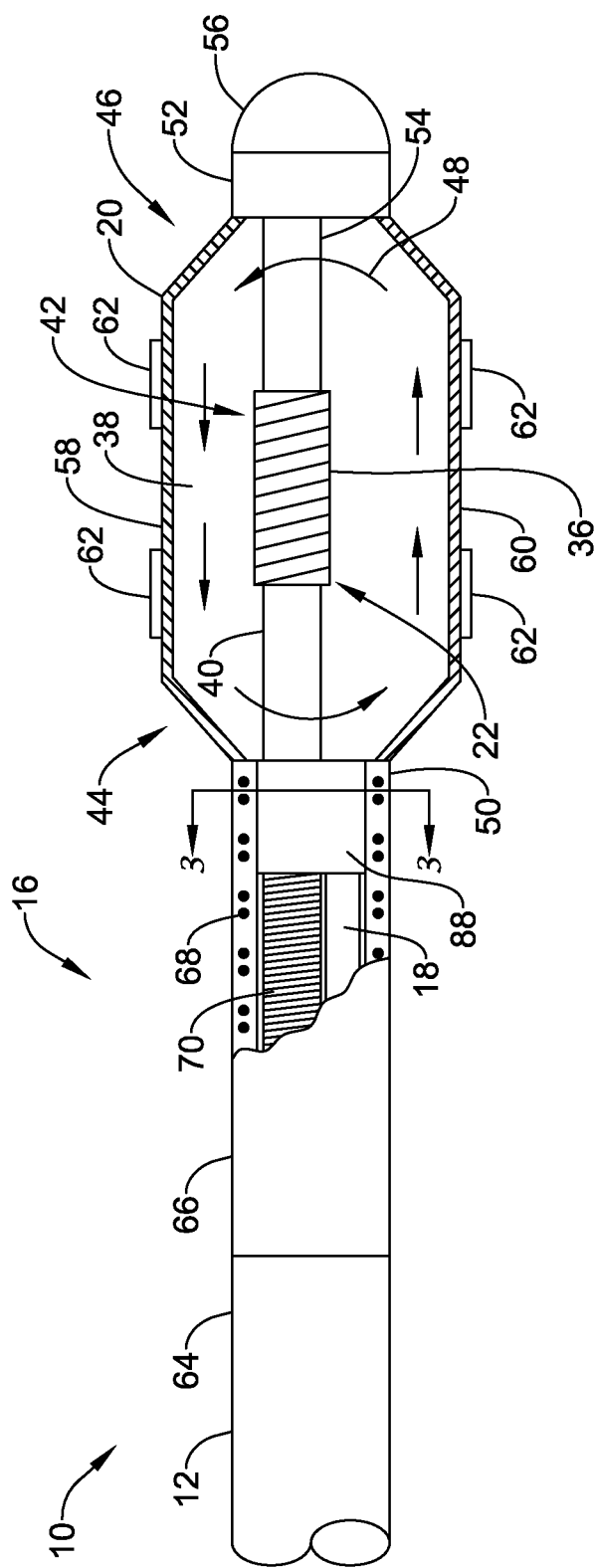
FIG. 2 is a partial cross-sectional view of the distal end region of the illustrative ablation device of FIG. 1.

FIG. 2 is a partial cross-sectional view showing the distal section of the ablation device of FIG. 1 in greater detail. As can be further seen in FIG. 2, and in some embodiments, the electrode assembly 22 comprises at least one RF electrode 36 located within an interior space 38 of the balloon 20. The RF electrode 36 is fixedly secured to a distal end region 42 of the steering tube 40 (e.g., using a suitable adhesive at both ends of the electrode 36), and is electrically coupled to the RF generator 34. In the embodiment of FIG. 2, the RF electrode 36 comprises a helically wound member made from a suitably conductive metal such as platinum gold, stainless steel, cobalt alloys, or other non-oxidizing materials, and is electrically coupled to the RF generator 34 via one or more conductor wires 80 (see FIG. 3) within the elongate shaft 12. The configuration of the RF electrode 36 can vary from that shown, however. For example, the RF electrode 36 can comprise a tubular member, coil, ring, flat ribbon, or other suitable shape. In some embodiments, the electrode assembly 22 can include multiple electrodes 36 as part of either a bipolar RF ablation system, or as part of a unipolar system with multiple electrodes.

The device 10 includes at least one fluid lumen 18 for transmitting pressurized fluid 30 to the interior space 38 of the balloon 20. In the embodiment of FIG. 2, the device 10 includes a fluid lumen 18, generally offset from the center of the elongate shaft 12, which extends longitudinally through the shaft 12. In some embodiments, the fluid lumen 18 terminates at the proximal end region 44 of the balloon 20. However, this is not required. In some instances, the fluid lumen 18 may extend distally into the interior space 38 of the balloon 20. In some embodiments, the same fluid lumen 18 can be used for both inflating and deflating the balloon 20. In other embodiments, separate fluid lumens are used for inflating and deflating the balloon 20, one example of which is shown in more detail in FIG. 3. Such a configuration can provide continuous infusion and evacuation of fluid within the balloon 20 to maintain both a controlled operating pressure and temperature range within the balloon 20. In one embodiment, multiple fluid lumens within the shaft 12 may permit the electrically conductive fluid 30 to be recirculated through the device 10 during the ablation procedure, as shown by arrows 48. The fluid 30 can also include a contrast medium to facilitate visualization of the balloon 20 under fluoroscopy.

In the embodiment of FIG. 2, the proximal end region 44 of the balloon 20 is coupled to the distal section 16 of the shaft 12 at or near the distal shaft end 50, and is inflatable from an initial, collapsed position having a low-profile that facilitates traversal of the device 10 through the body, to a second, expanded position that contacts and engages the body tissue to be ablated. In some instances, the balloon 20 extends linearly from the distal shaft end 50. For example, the balloon 20 may have a length extending from the proximal end region 44 to the distal end region 46 and a maximum cross-sectional width in the expanded configuration. The length of the balloon 20 may be greater than the cross-sectional width. The balloon 20 may be constructed and shaped to allow for a simple balloon geometry that may increase the durability of the balloon 20 as well as improve the folding profile. The balloon 20 is coupled at its distal end region 46 to a distal mount 52. The distal mount 52 may be fixedly secured to a distal end region 54 of the steering tube 40. In some instances, the distal mount 52 may include a platinum tip 56, although this is not required.

In certain embodiments, the balloon 20 has a composite structure formed from different polymeric materials, which helps to direct and focus the RF energy from the RF electrode 36 into the body tissue. Such a composite balloon structure is disclosed in U.S. patent application Ser. No. 13/616,161, entitled "Ablation Device with Ionically Conductive Balloon," which is fully and expressly incorporated herein by reference. In one embodiment, for example, a first longitudinally extending portion 58 of the balloon 20 may be a non-conductive region made from a hydrophobic polymer and a second longitudinally extending portion 60 of the balloon 20 may be a conductive region made from a hydrophilic polymer. In some instances, conductive region 60 of the balloon 20 may be laterally offset from the central axis of the balloon 20 and may extend along the length, or a portion of the length, of the balloon 20. This may define a conductive region 60, and hence a treatment region, extending generally parallel to a longitudinal axis of the balloon 20.

The polymer of the non-conductive region 58 can be non-ionically conductive and the polymer of the conductive region 60 can be ionically conductive. In some embodiments, for example, the composite balloon structure can comprise a non-conductive region 58 made from a hydrophobic polyurethane material and a conductive region 60 made from a hydrophilic polyurethane material such as TECOPHILIC 60D®, available from Lubrizol, Wickliffe, Ohio. TECOPHILIC® is a polyether-based aliphatic polyurethane and exhibits sufficient elasticity so as to be capable of stretching substantially beyond its equilibrium dimensions when the balloon 20 is inflated. Other polymeric materials can also be used to impart differing hydrophilic characteristics different portions of the balloon 20. As used herein, the term "hydrophilic" indicates that the polymer, when in contact with an aqueous solution, can absorb a quantity of water while still maintaining its structural integrity.

It is contemplated that different regions and/or varying size regions of the balloon 20 may be made of a hydrophilic material depending on the desired application. For example, while the non-conductive and conductive portions 58, 60 have been described as extending longitudinally along a length of the balloon 20, in some instances, the portions 58, 60 may extend around a portion of the circumference of the balloon 20 or in other patterns, as desired. In some instances, the entire balloon 20 may be formed from a hydrophilic material. When it is desired to direct and focus the RF energy from the RF electrode 36 to a particular location, an additional mask may be used. For example, in some instances, a masking agent, such as a non-conductive material or other material suitable for preventing the flow of RF energy from a portion of the balloon 20, may be applied directly to a portion of the outer surface of the balloon 20 to create a conductive region 60. In other instances, the balloon 20 may be disposed within a tubular structure (not explicitly shown) having one or more cut-out regions for allowing RF energy to pass while preventing RF energy from passing at other regions. These are just examples.

When inflated with the electrically conductive fluid 30, the conductive region 60 of the composite balloon 20 is rendered conductive by hydration due to the ionic content of the fluid 30 when the RF energy is supplied to the RF electrode 36. As a result, electrical current is transmitted through the fluid 30 and into the tissue in contact with the conductive region 60 of the balloon 20. In some cases, current passes through all areas of the balloon material that are hydrophilic but does not pass through areas of the balloon that are hydrophobic, non-conductive, or masked.

The composite balloon structure can be formed using a number of different techniques. For example, the different sections 58, 60 of the balloon 20 can be formed by separately dip-coating each section of the balloon 20 on a mandrel that has a defined size and shape. The balloon 20 can also be formed using other techniques, such as by spin-coating in a hollow mold or by injection or blow-molding.

In some embodiments, the device 10 may further include one or more temperature sensing elements (not explicitly shown) that can be used to sense the temperature of fluid 30 within the balloon 20. In certain embodiments, a temperature sensing element such as a thermocouple or thermistor is coupled to an inner surface of the balloon 20. In other embodiments, the balloon 20 may include one or more printed circuit electrodes 62 positioned around the outer and/or inner surface of the balloon 20. The one or more printed circuit electrodes 62 may provide additional information related to, but not limited to, balloon to tissue contact and lesion formation to better control the ablation procedure. In these or other embodiments referenced herein, the intensity of ablation therapy (e.g., power) can be automatically modulated based on the measured temperature to limit the temperature of the tissue undergoing ablation. Such a configuration can provide protection from steam pops, where a small gaseous rupture in tissue can otherwise be created by water in the tissue turning into steam when the temperature reaches 100° C. or greater.

The elongate shaft 12 may include a proximal portion 64 and a distal portion 66. The proximal portion 64 may be structured to maximize torque transmission and may include a typical braided structure, or the like. For example, in some instances, the proximal portion 64 may include reinforcing structures such as, but not limited to, coils, hypotubes, cut hypotubes, etc. The distal portion 66 may be softer and more flexible than the proximal portion 64 to allow the distal portion 66 to move more easily within a steerable or fixed sheath. Similar to the proximal portion 64, the distal portion 66 may include a reinforcement layer 68, such as a braided structure, coils, hypotubes, cut hypotubes, etc. While both the proximal and distal portions 64, 66 may include a reinforcing layer such as, a braided layer or the like, it is contemplated that the reinforcing layers may be structured the same or differently to provide the desired characteristics.

Figure 3:
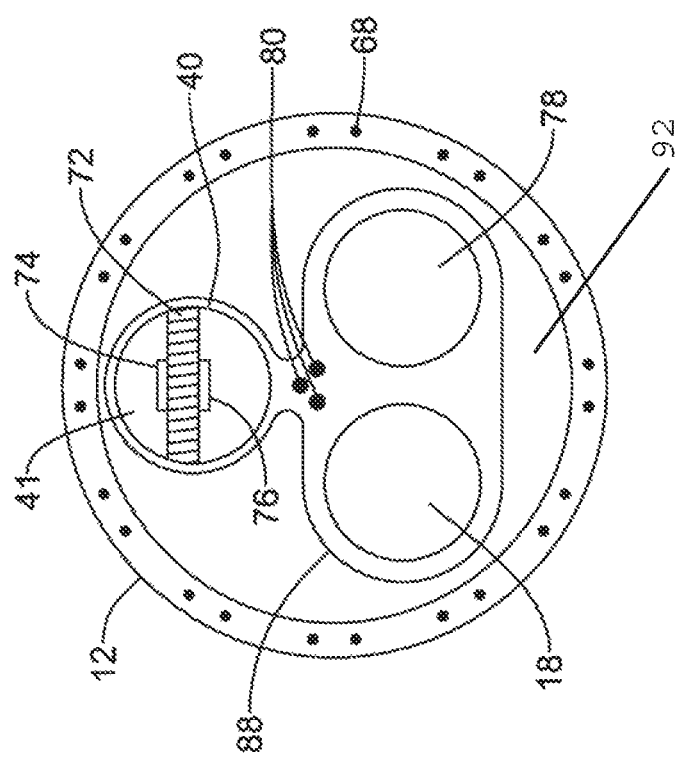
FIG. 3 is a cross-sectional view taken at line 3-3 of the illustrative ablation device of FIG. 2.
Figure 4:
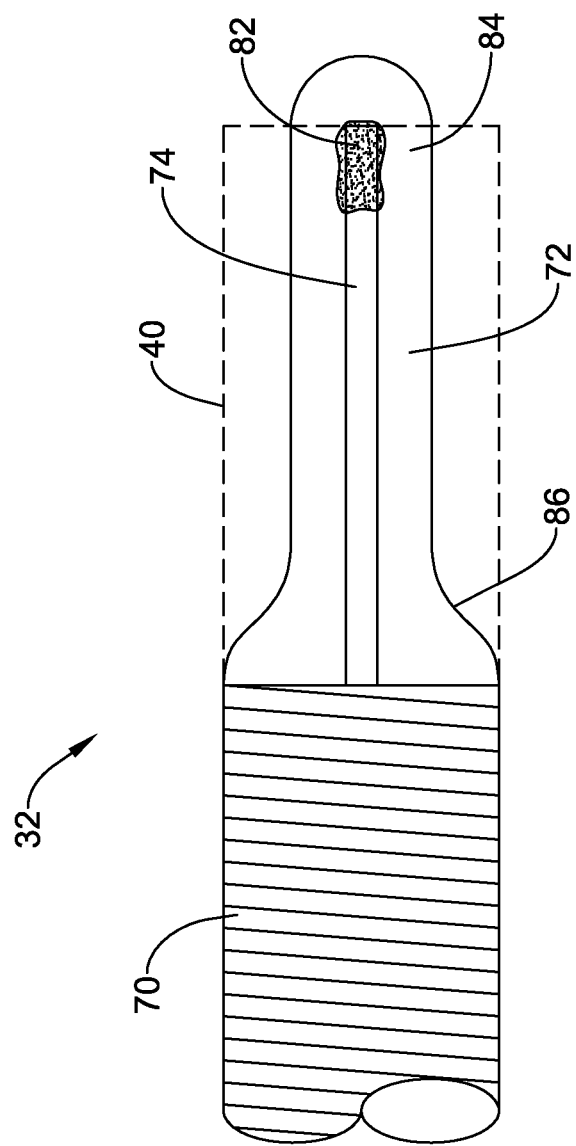
FIG. 4 is a schematic view of an illustrative steering mechanism.

As discussed above, the ablation device 10 also includes a steering mechanism 32. Details of an example steering mechanism 32 will now be discussed with reference to FIGS. 2-4. FIG. 3 is a cross-sectional view of the elongate shaft 12 taken at line 3-3 in FIG. 2. FIG. 4 is a schematic view of a portion of an illustrative steering mechanism 32. The steering mechanism 32 includes a steering tube 40 defining a lumen 41 therein. The steering tube 40 may extend from the proximal section 14 of the elongate shaft 12 to the distal mount 52. A center support 72 is disposed within the lumen 41 of the steering tube 40. The center support 72 may include a tapered region 86 which may enable very tight steering of the distal section 16 and balloon 20. For example, the longitudinal location of the tapered region 86 may generally define the articulation point of the device 10. Thus, the tapered region 86 may be positioned adjacent to the region of the balloon 20 or elongate shaft 12 where bending is desired. The tight steering may allow the balloon 20 to bend to approximately 90° or greater relative to the longitudinal axis of the elongate shaft 12 in two opposite directions. The steering mechanism 32 may further include a first pull wire 74 positioned on a first side of the center support 72 and a second pull wire 76 positioned on a second side of the center support 72. The proximal ends of the pull wires 74, 76 may be secured to the actuation mechanism in the handle 24 of the device 10. A distal end of the pull wires 74, 76 are secured to the center support 72 adjacent to the distal end of the steering tube 40 through a solder joint 82 or other suitable bonding mechanism. Actuation of the actuation mechanism will cause the balloon 20 to deflect relative to the longitudinal axis of the elongate shaft 12. The steering mechanism 32 may further include a compression coil 70 positioned along at least a portion of the steering tube 40. In some instances, the compression coil 70 may be disposed along an exterior surface of the steering tube 40. In other instances, the compression coil 70 may be disposed within the lumen 41 of the steering tube 40. In yet other embodiments, the compression coil 70 may be embedded within the wall of the steering tube 40.

As shown in FIG. 3, the elongate shaft 12 may include a first fluid lumen 18 and a second fluid lumen 78. In some instances, the first fluid lumen 18 may be used for providing fluid to the balloon 20 while the second fluid lumen 78 may evacuate fluid from the balloon 20. Such a configuration can provide continuous infusion and evacuation of fluid within the balloon 20 to maintain both a controlled operating pressure and temperature range within the balloon 20. Multiple fluid lumens 18, 78 within the shaft 12 may permit the electrically conductive fluid 30 to be recirculated through the device 10 during the ablation procedure.

In some embodiments, the steering tube 40 and fluid lumens 18, 78 may be formed as a unitary structure or insert 88 separate from the elongate shaft 12 that is subsequently disposed within a lumen 92 of the elongate shaft 12. It is contemplated that the insert 88 may be secured to the elongate shaft 12 at various points along the length thereof. For example, the insert 88 may be fixedly secure to the proximal and distal sections 14, 16 of the elongate shaft. In other instances, all of or at least one of the steering tube 40 and fluid lumen 18, 78 may be formed as a unitary structure with the elongate shaft 12.

FIG. 5 illustrates a side view of the illustrative ablation device 10 illustrating an example deflective range of the ablation device 10. As discussed above, a steerable sheath 90 may be used in cooperation with the ablation device 10 to facilitate advancement of the device 10 to the desired treatment location. In the treatment of paroxysmal atrial fibrillation, for example, the clinician may insert the sheath 90 and ablation device 10 into a main vein or artery (e.g., a femoral artery), and advance the assembly through the vasculature into position within a heart chamber or cardiac vessel to be treated (e.g., a pulmonary vein). However, a steerable sheath 90 is not required. In some embodiments, the sheath 90 may not have steering capabilities. Once the sheath 90 and ablation device 10 have been advanced to the desired treatment region the ablation device 10 is advanced out of the sheath and an electrically conductive fluid 30 is infused into the balloon 20. Once the balloon 20 has been expanded, the actuation mechanism may be articulated to position the balloon 20 such that the conductive region 60 is in contact with the target tissue. In some instances, the balloon 20 may be positioned prior to expanding the balloon 20. In some instances, the distal tip 56 of the balloon 20 may be deflected such that the distal end region 46 of the balloon 20 is disposed at an angle, such as generally orthogonal, to a longitudinal axis L of the device 10 in an undeflected state. However, it is contemplated that the distal end region 46 of the balloon 20 can be deflected to any angle desired, such as, but not limited in the range of about 1° to about 90° from the longitudinal axis L. In some instances, the distal end region 46 of the balloon 20 can be deflected to angles greater than 90° from the longitudinal axis L such that the distal end region 46 of the balloon 20 begins to bend back on itself. These are just examples and are not intended to limit the deflection of the device 10 to a particular value. Rather, the degree of the deflection may be selected by the clinician to provide the best contact between the conductive region 60 and the target tissue. While FIG. 5 illustrates the articulation point of the device 10 at an intermediate region of the balloon 20, it is contemplated that the steering mechanism 32 may be configured to place the articulation point at the desired location. For example, the articulation point may be located closer to the distal end region 46 of the balloon, closer to the proximal end region 44 of the balloon, or along the elongate shaft 12, as desired.

Once the balloon 20 is in position and expanded, the RF generator 34 can then be set to activate the electrode 36, causing energy to flow from the electrode 36 to the conductive region 60 of the balloon 20 through conduction through the fluid and balloon material. The clinician may then form a relatively wide lesion on the tissue by contacting the conductive region 60 of the balloon 20 with the tissue. In some instances, the lesion may have a generally crescent or bean shape that conforms to the outer surface of the balloon. Once the desired lesion has been obtained, the RF generator 34 may be deactivated and the balloon 20 repositioned and ablation repeated. Ablation may be performed in as many locations as desired to achieve the desired effect. In some instances, the ablation procedure may be repeated as many times as necessary to form a lesion around the entire circumference of a vessel. It is contemplated that as few as three to four lesions may be required to form the desired lesion in the treatment of paroxysmal atrial fibrillation.

Those skilled in the art will recognize that the present invention may be manifested in a variety of forms other than the specific embodiments described and contemplated herein. Accordingly, departure in form and detail may be made without departing from the scope and spirit of the present invention as described in the appended claims.

What is claimed is:

1. An ablation device for treating body tissue, comprising:
   an elongate shaft having a proximal section, a distal section, and at least one fluid lumen
      configured to receive an electrically conductive fluid;
   a steering mechanism disposed within the elongate shaft, the steering mechanism comprising:
      a steering tube;
      a center support; a first pull wire positioned on a first side of the center support; and
      a second pull wire positioned on a second side of the center support;
   an inflatable balloon coupled to the distal section of the shaft and including an interior section in fluid communication with the at least one fluid lumen for actuating the balloon between a collapsed state and an expanded state, wherein at least a portion of the balloon comprises a hydrophilic polymeric material; and
   at least one electrode located within the interior section of the balloon,
   wherein the center support includes a tapered region disposed within the balloon, the tapered region including a first outer diameter and a second outer diameter and a transition from the first diameter to the second diameter defining an articulation point of the device.

2. The ablation device of claim 1, wherein at least a portion of the balloon comprises a hydrophobic polymer material.

3. The ablation device of claim 1, further comprising at least one additional fluid lumen for circulating fluid through the device.

4. The ablation device of claim 1, wherein the balloon has a length and a cross-sectional width, the length being greater than the width.

5. The ablation device of claim 1, wherein the steering mechanism is configured to bend the balloon approximately 90° or greater relative to a longitudinal axis of the elongate shaft in two opposite directions.

6. The ablation device of claim 1, further comprising a compression coil extending along at least a portion of the steering tube.

7. The ablation device of claim 1, further comprising one or more printed circuit electrodes disposed on an outer surface of the balloon.

8. The ablation device of claim 1, wherein the steering tube extends from the proximal section of the elongate shaft to a distal end of the balloon.

9. An ablation device for treating body tissue, comprising:
   an elongate shaft having a proximal section, a distal section, a first fluid lumen
      configured to receive an electrically conductive fluid and a second fluid lumen;
   a steering mechanism disposed within the elongate shaft, the steering mechanism comprising:
      a steering tube;
      a center support; a first pull wire positioned on a first side of the center support; and
      a second pull wire positioned on a second side of the center support;
   an inflatable balloon coupled to the distal section of the shaft and including an interior section in fluid communication with first and second fluid lumens for actuating the balloon between a collapsed state and an expanded state, wherein at least a first portion of the balloon comprises a hydrophilic polymeric material and a second portion of the balloon comprises a hydrophobic polymeric material; and
   at least one electrode located within the interior section of the balloon,
   wherein the center support includes a tapered region disposed within the balloon, the tapered region including a first outer diameter and a second outer diameter and a transition from the first diameter to the second diameter defining an articulation point of the device.

10. The ablation device of claim 9, further comprising a sheath.

11. The ablation device of claim 10, wherein the sheath is steerable.

12. The ablation device of claim 9, wherein the steering mechanism is configured to bend the balloon approximately 90° or greater relative to a longitudinal axis of the elongate shaft in two opposite directions.

13. The ablation device of claim 9, further comprising a compression coil extending along at least a portion of the steering tube.

14. The ablation device of claim 9, wherein the steering tube extends from the proximal section of the elongate shaft to a distal end of the balloon.

15. An ablation device for treating body tissue, comprising:
   a sheath;
   an elongate shaft having a proximal section, a distal section, a first fluid lumen and a second fluid lumen;
   a steering mechanism disposed within the elongate shaft, the steering mechanism comprising:
      a steering tube defining a lumen therethrough;
      a center support extending through the steering tube lumen, the center support including a tapered region;
      a first pull wire positioned on a first side of the center support; a second pull wire positioned on a second side of the center support; and
      a compression coil extending along at least a portion of the steering tube, wherein the compression coil is disposed along the exterior of the steering tube or embedded within the wall of the steering tube;
   an inflatable balloon coupled to the distal section of the shaft and including an interior section in fluid communication with the first and second fluid lumens for actuating the balloon between a collapsed state and an expanded state, wherein at least a first portion of the balloon comprises a hydrophilic polymeric material; and at least one electrode located within the interior section of the balloon.

16. The ablation device of claim 15, wherein the steering mechanism is configured to bend the balloon approximately 90° or greater relative to a longitudinal axis of the elongate shaft in two opposite directions.

17. The ablation device of claim 15, further comprising one or more printed circuit electrodes disposed on an outer surface of the balloon.

18. The ablation device of claim 15, wherein the steering tube extends from the proximal section of the elongate shaft to a distal end of the balloon.

19. The ablation device of claim 15, wherein the tapered region is disposed within the balloon, the tapered region including a first outer diameter and a second outer diameter and a transition from the first diameter to the second diameter defining an articulation point of the device.

\* \* \* \* \*